United States Patent [19]

Pews et al.

[11] Patent Number: 4,937,397

[45] Date of Patent: Jun. 26, 1990

[54] PREPARATION OF HALOFLUOROBENZENES

[75] Inventors: R. Garth Pews; James A. Gall, both of Midland, Mich.

[73] Assignee: The Dow Chemical Company, Midland, Mich.

[21] Appl. No.: 276,713

[22] Filed: Nov. 28, 1988

[51] Int. Cl.$^5$ .................. C07C 17/20; C07C 25/02
[52] U.S. Cl. ................................ 570/147; 570/127
[58] Field of Search ........................ 570/147, 144

[56] References Cited

U.S. PATENT DOCUMENTS

| | | | |
|---|---|---|---|
| 3,574,775 | 4/1971 | Fuller | 260/650 |
| 4,369,145 | 1/1983 | Souls | 570/147 |
| 4,590,315 | 5/1986 | Moul et al. | 570/127 |

FOREIGN PATENT DOCUMENTS

| | | | |
|---|---|---|---|
| 228436 | 11/1985 | Japan | 570/147 |
| 1062301 | 3/1967 | United Kingdom | 570/144 |

OTHER PUBLICATIONS

Shiley et al. "J. Fluorine Chem.", pp. 2,19 (1972/73).
Starr et al. "Chemistry & Industry", 1328, Jul. 21, 1962.

*Primary Examiner*—J. E. Evans
*Attorney, Agent, or Firm*—Craig E. Mixan; Ronald G. Brookens

[57] ABSTRACT

Chlorofluorobenzenes and difluorobenzenes are prepared by contacting a dichlorobenzene with an effective amount of KF or CsF in a polar aprotic solvent at an elevated temperature under substantially anhydrous conditions. The product can be removed as it is formed or the reaction may be run at the autogenous pressures generated by the reaction mixture in a sealed reactor.

15 Claims, No Drawings

PREPARATION OF HALOFLUOROBENZENES

FIELD OF INVENTION

The present invention relates to the preparation of fluorobenzenes from the corresponding chlorobenzenes. More particularly, the present invention is directed to the preparation of chlorofluorobenzenes and difluorobenzenes using potassium fluoride (KF) and/or cesium fluoride (CsF) as the fluorinating agent.

BACKGROUND OF THE INVENTION

Halofluorobenzenes are useful intermediates for the manufacture of various dyes, agricultural pesticides, pharmaceutical and industrial compounds. For example, o-bromofluorobenzene may be converted to 3-fluorosalicylaldehyde for use in preparing oxygen absorbing solid state chelates such as "Fluomine" [cobalt bis(3-fluorosalicylaldehyde)ethylenediimine].

Conventional methods of preparing halofluoroaromatic compounds are based primarily on diazotization routes involving a number of steps. In U.S. Pat. No. 4,476,320, for example, halofluoroaromatic compounds were prepared by (a) diazotizing the corresponding haloaromatic amine compound to the diazonium salt, and (b) decomposing the salt to the desired product

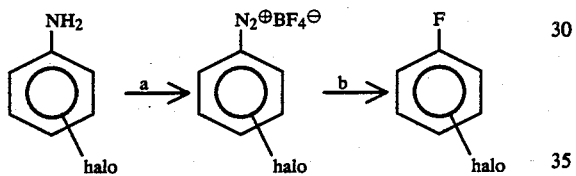

A similar scheme was employed in U.S. Pat. No. 3,950,444 and in Japanese Kokai Tokkyo Koho JP No. 59 67,232.

Alternatively, halofluorobenzenes have been prepared by the halogenation of fluorobenzenes, but the fluorobenzene starting materials are themselves usually prepared by the above-mentioned diazonium chemistry.

Of primarily laboratory interest, several techniques for the fluorination of halobenzenes have recently been disclosed. These procedures include fluorination with fluorine atoms (*J.FluorineChem.*, 3, 397 (1973)), with acetyl hypofluorite (*J.Org.Chem.*, 51, 1886 (1986)) and with AgF$_2$ (*J.Org.Chem.*, 45, 3597 (1980)).

Although highly fluorinate aromatic compounds can be prepared from perhalogenated aromatic compounds or perhalogenated aromatic compounds containing one or more electron-withdrawing substituents by the action of alkali metal fluorides, it was believed that this reaction was of preparative interest only for producing completely halogenated compounds and that reactions between incompletely halogenated aromatic compounds and KF were accompanied by numerous side reactions and poor yields. (See, for example, Yakobson et al. in Synthesis, 652, October 1976).

Shiley et al. in *J.FluorineChem.*, 2, 19 (1972) disclose the fluorination of trichlorobenzenes with KF in dimethyl sulfone. Moderate yields (56 percent) of 1,3,5-trifluorobenzene were obtained, but only poor yields (less than 15 percent) of the 1,2,3- and the 1,2,4-trifluorobenzenes were achieved. In testing the stability of fluorobenzenes in halogen-exchange conditions milder than those required to produced the fluorobenzenes from their intermediates, Shiley et al. concluded that it would be difficult to find conditions for the halogen-exchange reaction that would be more conducive to better yields of the fluorobenzenes.

SUMMARY OF THE INVENTION

We have now found that, contrary to these beliefs, incompletely fluorinated benzenes can be prepared in good yield by the action of KF or CsF on the corresponding chlorinated benzenes. The present invention is directed to a method for preparing a chlorofluorobenzene or difluorobenzene of the formula

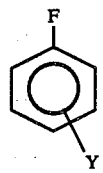

which comprises contacting a dichlorobenzene or chlorofluorobenzene of the formula

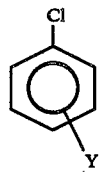

wherein
Y is Cl or F,
with effective amount of KF or CsF under substantially anhydrous conditions in a suitable polar aprotic solvent at a temperature so that fluorine exchange readily occurs, and recovering the chlorofluorobenzene or the difluorobenzene from the reaction mixture.

Surprisingly, the present invention allows for the preparation of chlorofluorobenzenes and difluorobenzenes from the corresponding dichlorobenzenes in good yield with a minimum of side reactions. The conversion may be effectively accomplished with both CsF and the much less expensive KF.

DETAILED DESCRIPTION OF THE INVENTION

The conversion of a dichlorobenzene (I) to a difluorobenzene (III) is a stepwise process which involves the intermediacy of a singularly fluorine-exchanged compound (II; chlorofluorobenzene),

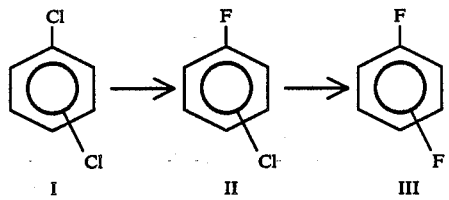

Optionally, the reaction can be conducted in a fashion so that the singularly fluorine-exchanged chlorofluorobenzene is obtained as the major product.

KF and CsF are the fluorinating agents employed in the present reaction and are commercially available compounds. substantially anhydrous and finely-divided KF or CsF are preferred. Amorphous and or spray-dried forms are particularly preferred. Substantially anhydrous KF and CsF can be prepared, for example, by drying in vacuo at 140°–250° C. for several hours.

Dichlorobenzenes are also commercially available compounds.

Suitable polar aprotic diluents of the present invention include N-methyl pyrrolidinone (NMP), N-cyclohexyl pyrrolidinone (NCHP), 1,3-dimethyl-2-imidazolidinone (DMI) and 1,3-dimethyl-3,4,5,6-tetrahydro-2-(1H)pyrimidone (DMTHP).

Optionally, the reaction may be conducted in the presence of
(a) and acid scavenger, such as, an alkali metal carbonate, and/or in the case of employing KF as the fluorinating agent,
(b) a phase-transfer catalyst.

The present reaction is conducted under substantially anhydrous conditions at elevated temperatures of from about 240° to about 350° C. Preferred temperature ranges are from about 240° to about 330° C. when CsF is used, and from about 290° to about 350° C. when KF is used.

Pressures of from atmospheric to greater than atmospheric are typically employed. For CsF, which is more reactive than KF, it is often convenient to operate at atmospheric pressure. For KF, which is less expensive than but also less reactive than CsF, it is preferred to operate at the autogenous pressure generated by the diluent, starting material and product in a sealed reactor at the preferred reaction temperatures of 290° to 350° C. Such pressures typically range from slightly above atmospheric to about 500 pounds per square inch (psi) and depend upon the volume of the reactor. Optionally, the reaction can be run under pressure in a suitably designed reactor equipped with a distillation column so the product can be removed as formed.

Water is detrimental to the reaction and substantially anhydrous reaction conditions are preferred. By substantially anhydrous is meant that the reaction medium contains less than about 500 parts per million (ppm) water. Perferably the reaction medium contains less than about 150 ppm water. Substantially anhydrous conditions may be achieved employing standard drying techniques. For example, a typical laboratory reactor can be dried by distilling the polar aprotic solvent under a vacuum before addition of the reactants. Optionally, a small amount (5–10 percent by weight of the polar aprotic solvent) of a non-polar solvent such as an aromatic hydrocarbon (toluene, xylene, etc.) may be added to the polar aprotic solvent to aid in the removal of water by azeotropic distillation. Residual water in the reactor system is also often removed by azeotropic distillation.

The amount of polar aprotic solvent is not critical, but it is advantageous to employ enough solvent to keep the starting material in solution at reaction temperatures, generally from about 2 to about 25 parts by weight of the solvent per part by weight of the chloroaromatic starting material. The relative proportions of reactants to be employed are not critical because some of the product will be formed when employing any proportion of reactants. The reaction consumes the reactants, however, in the ratio of one mole of fluorinating agent per mole of exchangeable chlorine atoms present in the starting material. For example, with o-dichlorobenzene as the starting material, about 2 molar equivalents of KF or CsF per mole of starting material are consumed if o-difluorobenzene is the desired product. If o-chlorofluorobenzene is desired, only one molar equivalent of KF or CsF per mole of o-dichlorobenzene will be consumed. Usually from about 1.0 to about 4.0 moles of KF or CsF are employed per mole of exchangeable chlorine in the chlorobenzene starting material.

The present reaction is typically conducted in the presence of agitation sufficient to maintain an essentially uniform dispersion of the reactants in the solvent.

Catalysts are optionally employed to increase the reaction rate. Suitable catalysts include phase-transfer catalysts. The catalyst is added to the present reaction mixture in an amount of from about 0.0001 to about 0.1 mole per mole of chlorobenzene starting material, advantageously from about 0.001 to about 0.075 molar equivalents and preferably from about 0.01 to about 0.05 molar equivalents.

Phase-transfer catalysts are well-known compounds and include (a) quaternary phosphonium salts containing 10 or more carbon atoms and (b) macrocyclic polyethers commonly known as crown ethers. Suitable crown ether catalysts include 18-crown-6; dicyclohexano-18-crown-6; dibenzo-18-crown-6; 15-crown-5. A related species, tris(3,6-dioxa-heptyl)amine is also efficacious. Suitable quaternary phosphonium salts include the tetra-n-alkylphosphonium salts. The anion of the phosphonium salts is $F^\ominus$, which may be derived from any anion which readily converts to $F^\ominus$, such as, for example, $Cl^\ominus$, $Br^\ominus$, $I^\ominus$, $OH^\ominus$, $OAc^\ominus$, etc., under the reaction conditions.

Acid scavengers are optionally employed in the present reaction to consume or inactivate traces of HCl or HF which may be present or generated during the reaction. Suitable acid scavengers include alkali metal carbonates such as anhydrous $K_2CO_3$ and anhydrous $Na_2CO_3$. A preferred acid scavenger is anhydrous $K_2CO_3$. The acid scavengers are added to the present reaction mixture in an amount of from about 0.001 to about 0.1 mole per mole of chlorobenzene starting material. Preferably, from about 0.03 to about 0.05 molar equivalents are employed.

The chlorofluorobenzene or difluorobenzene product can be recovered from the reaction mixture by conventional techniques such as extraction and/or distillation. Preferably, the product is removed from the reaction mixture as it is formed. Optionally, the reactant compound may be added as the product is removed.

The product may be separated from starting material and/or intermediate by fractional distillation.

In carrying out the present reaction, neither the rate nor the order of addition of the reactants is critical. Usually, the solvent and fluorinating agent are added to an appropriate reaction vessel, and the reaction is dried by distilling a small portion of the solvent. The starting material of percursor compound is then added to the reaction vessel. The reaction mixture is then heated to a temperature high enough to maintain a satisfactory reaction rate. The product may be recovered from the reaction mixture after completion of the reaction by extraction and or distillation. Alternatively, the product may be removed from the reaction mixture by fractional distillation as it is formed. If an acid scavenger, a non-polar solvent, or catalyst is employed in the reaction, then they are advantageously added to the solvent/fluorinating agent mixture prior to drying the reactor vessel.

The following examples illustrate the practice of the present invention and should not be construed as limiting.

either alone or in tandem with a mass spectrometer. The experimental conditions and the results of these experiments are summarized in Table I.

TABLE I

Fluorine-Exchange on o-Dichlorobenzene

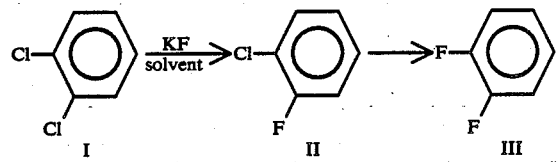

| Exp. No. | Temp °C. | Time hr | KF (Mol) | I (Mol) | KF/I | Reaction Composition | | | I/II/III % | Mat. Bal. | Solvent |
|---|---|---|---|---|---|---|---|---|---|---|---|
| | | | | | | I (Mol) | II (Mol) | III (Mol) | | | |
| 1 | 290/330 | 19/16.5 | 0.8 | 0.2 | 4 | 0.045 | 0.123 | 0.016 | 24/67/9 | 92.00% | NMP |
| 2 | 350 | 24 | 0.8 | 0.2 | 4 | 0.023 | 0.123 | 0.021 | 14/74/12 | 83.50% | NMP |
| 3 | 350 | 18 | 0.8 | 0.2 | 4 | 0 | 0.009 | 0.012 | 0/43/57 | 10.50% | NMP |
| 4 | 350 | 24 | 0.8 | 0.203 | 4 | 0.012 | 0.112 | 0.032 | 8/72/20 | 76.84% | NMP |
| 5 | 340 | 64 | 0.8 | 0.2 | 4 | 0 | 0.025 | 0.04 | 0/38/62 | 32.50% | NMP |
| 6 | 300 | 70 | 0.4 | 0.2 | 2 | 0.049 | 0.119 | 0.012 | 27/66/7 | 90.00% | NMP |
| 7 | 290 | 66 | 0.8 | 0.4 | 2 | 0.29 | 0.105 | 0 | 73/27/0 | 98.75% | NMP |
| 8 | 320 | 24 | 0.8 | 0.2 | 4 | 0.068 | 0.11 | 0.007 | 37/59/4 | 92.50% | NMP |
| 9 | 310 | 24 | 0.8 | 0.2 | 4 | 0.092 | 0.092 | 0.001 | 50/50/0 | 92.50% | NMP |
| 10 | 320 | 24 | 0.8 | 0.2 | 4 | 0.163 | 0.028 | 0 | 85/15/0 | 95.50% | NCHP |
| 11 | 320 | 24 | 0.8 | 0.2 | 4 | 0.049 | 0.093 | 0.011 | 32/61/7 | 76.50% | DMTHP |
| 12 | 300 | 24 | 0.4 | 0.1 | 4 | 0.063 | 0.03 | 0.001 | 67/32/1 | 94.00% | DMTHP |
| 13 | 300 | 24 | 0.4 | 0.1 | 4 | 0.058 | 0.032 | 0 | 64/36/0 | 90.00% | DMI |
| 14 | 300 | 24 | 0.2 CsF | 0.05 | 4 | 0 | 0 | 0.028 | 0/0/100 | 56.00% | DMI |
| 15 | 300 | 24 | 0.2 CsF | 0.05 | 4 | 0 | 0.002 | 0.015 | 0/12/88 | 34.00% | NMP |

EXAMPLE 1

A series of experiments were conducted under pressue in a 600 milliliter (mL) Hastelloy "C" pressure reactor. The KF was dried in a vacuum oven at 150° C. for at least 24 hours (hr). Solvents were dried by distillation from calcium hydride. The solvent (250 mL), KF and o-dichlorobenzene were introduced into the pressure reactor with 5.0 grams (g) of mesitylene which served as an internal standard. The reactor was sealed and pressure tested. After the indicated times and temperatures, the reactor was cooled and vented and the reaction mixture was analyzed by gas chromatography,

EXAMPLE 2

The general procedure of Example 1 was repeated using a 300 mL or 600 mL Hastelloy C pressure reactor and substituting m-dichlorobenzene for the o-dichlorobenzene. The experimental conditions and results of these experiments are summarized in Table II.

TABLE II

Fluorine-Exchange on m-Dichlorobenzene

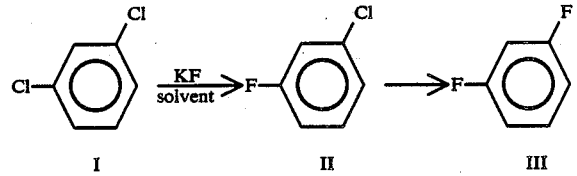

| Exp. No. | Temp °C. | Time hr | I (Mol) | KF (Mol) | KF/I | Reaction Composition | | | I/II/III % | Mat. Bal. | Solvent |
|---|---|---|---|---|---|---|---|---|---|---|---|
| | | | | | | I (Mol) | II (Mol) | III (Mol) | | | |
| 18 | 325 | 24 | 0.2 | 0.8 | 4 | 0.016 | 0.102 | 0.039 | 10/65/25 | 78.50% | NMP |
| 19 | 310 | 24 | 0.1 | 0.4 | 4 | 0.022 | 0.056 | 0.015 | 24/60/16 | 93% | NMP |
| 20 | 280 | 24 | 0.1 | 0.4 | 4 | 0.069 | 0.028 | 0.002 | 70/28/2 | 99% | NMP |
| 21 | 290 | 24 | 0.1 | 0.4 | 4 | 0.059 | 0.040 | 0.003 | 58/39/3 | 102% | NMP |
| 22 | 300 | 24 | 0.1 | 0.4 | 4 | 0.039 | 0.048 | 0.007 | 42/51/7 | 94% | NMP |
| 23 | 310 | 24 | 0.1 | 0.4 | 4 | 0.018 | 0.050 | 0.014 | 22/61/17 | 82% | NMP |
| 24 | 320 | 24 | 0.1 | 0.4 | 4 | 0.009 | 0.048 | 0.023 | 11/60/29 | 82% | NMP |

EXAMPLE 3

The general procedure of Example 1 was repeated substituting p-dichlorobenzene for the o-dichlorobenzene. The experimental conditions and results of these experiments are summarized in Table III.

TABLE III

Fluorine-Exchange on p-Dichlorobenzene

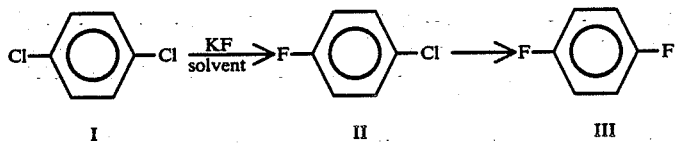

| Exp. No. | Temp °C. | Time hr | I (Mol) | KF (Mol) | KF/I | Reaction Composition | | | I/II/III % | Mat. Bal. | Solvent |
|---|---|---|---|---|---|---|---|---|---|---|---|
| | | | | | | I (Mol) | II (Mol) | III (Mol) | | | |
| 25 | 325 | 24 | 0.1 | 0.4 | 4 | 0.036 | 0.051 | 0.003 | 40/57/3 | 90% | NMP |

What is claimed is:

1. A process for preparing a chlorofluorobenzene or difluorobenzene of the formula

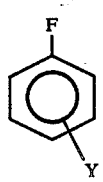

which comprises contacting a dihalobenzene of the formula

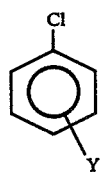

wherein
Y is F or Cl,
with an effective amount of KF under substantially anhydrous conditions is a solvent selected from the group consisting of N-methyl pyrrolidinone, N-cyclohexyl pyrrolidinone, 1,3-dimethyl-2-imidazolidinone and 1,3-dimethyl-3,4,5,6-tetrahydro-2-(1H)pyrimidone at a temperature from about 290° to about 350° C., and recovering the chlorofluorobenzene or the difluorobenzene from the reaction mixture.

2. The process of claim 1 in which Y is F.
3. The process of claim 2 in which Y is ortho to the exchanging Cl.
4. The process of claim 2 in which Y is meta to the exchanging Cl.
5. The process of claim 2 in which Y is para to the exchanging Cl.
6. The process of claim 1 in which Y is Cl.
7. The process of claim 6 in which Y is ortho to the exchanging chlorine.
8. The process of claim 6 in which Y is meta to the exchanging chlorine.
9. The process of claim 6 in which Y is para to the exchanging chlorine.
10. The process of claim 1 including the additional step of carrying out the reaction in the presence of a phase-transfer catalyst.
11. The process of claim 1 including the additional step of carrying out the reaction in the presence of an acid scavenger.
12. The process of claim 1 in which the reaction is run at the autogenous pressure generated by the reaction mixture in a sealed reactor.
13. A process for preparing o-chlorofluorobenzene which comprises contacting o-dichlorobenzene with from about 1.0 to about 4.0 molar equivalents of KF under substantially anhydrous conditions in a polar aprotic solvent selected from the group consisting of N-methyl pyrrolidinone, N-cyclohexyl pyrrolidinone, 1,3-dimethyl-2-imidazolidinone and 1,3-dimethyl-3,4,5,6-tetrahydro-2-(1H)pyrimidone at a temperature from about 290° to about 350° C. at an elevated pressure, and recovering the o-chlorofluorobenzene from the reaction medium.
14. The process of claim 13 in which the elevated pressure is from slightly above atmospheric to about 500 pounds per square inch.
15. The process of claim 13 in which the elevated pressure is the autogenous pressure generated by the reaction mixture in a sealed reactor.

* * * * *